United States Patent
Wahlbrink

[11] Patent Number: 5,925,881
[45] Date of Patent: Jul. 20, 1999

[54] INFRARED ABSORPTION MEASURING CELL

[75] Inventor: Günter Wahlbrink, Badendorf, Germany

[73] Assignee: Drägerwerk AG, Lübeck, Germany

[21] Appl. No.: 08/943,712

[22] Filed: Oct. 3, 1997

[30] Foreign Application Priority Data

Apr. 24, 1997 [DE] Germany .......................... 197 17 314

[51] Int. Cl.⁶ .................................................. G01N 21/61
[52] U.S. Cl. ............................................................ 250/343
[58] Field of Search ............................................ 250/343

[56] References Cited

U.S. PATENT DOCUMENTS

| | | | |
|---|---|---|---|
| 4,358,679 | 11/1982 | Lipoma . | |
| 5,341,214 | 8/1994 | Wong ...................................... | 356/437 |
| 5,550,375 | 8/1996 | Peters et al. ............................. | 250/343 |
| 5,625,189 | 4/1997 | McCaul et al. .......................... | 250/343 |

FOREIGN PATENT DOCUMENTS 63-50739   3/1988   Japan .............................. G01N 21/27

Primary Examiner—Constantine Hannaher
Assistant Examiner—Andrew Israel
Attorney, Agent, or Firm—McGlew & Tuttle, P.C.

[57] ABSTRACT

A measuring cell (1) for the analysis of a gas sample by infrared absorption, with a measuring path (2) accommodating the gas sample, which has opposite limiting surfaces (7, 9) enclosing the gas sample, wherein a focusing optical component (8) is present at the first limiting surface (7) and an infrared radiation source and a radiation receiver (4) are arranged in the area of the second limiting surface (9) such that a measuring beam (13) emitted by the radiation source (3) is directed onto the radiation receiver (4) through the optical component, shall be improved such that it be suitable for the detection of gases with a long absorption path. A mirror surface (12) active for the measuring path (2) is present in the area of the second limiting surface (9), and the geometry of the optical component (8) is dimensioned such that there is an at least fourfold pass of the measuring beam (13) in the measuring path (2), utilizing the reflection of the beam on the mirror surface (12).

14 Claims, 2 Drawing Sheets

INFRARED ABSORPTION MEASURING CELL

FIELD OF THE INVENTION

The present invention pertains generally to an absorption measuring cell and more particularly to a device for the analysis of a gas sample by means of infrared absorption, with a measuring path accommodating the gas sample, which has opposite first and second limiting surfaces enclosing the gas sample, wherein a focusing optical component is present at the first limiting surface and an infrared radiation source and a radiation receiver are arranged in the area of the second limiting surface, such that a measuring beam emitted by the radiation source is directed through the optical component onto the radiation receiver.

BACKGROUND OF THE INVENTION

A measuring cell of this general type has become known from U.S. Pat. No. 4,358,679. In the prior-art measuring cell, the gas sample to be analyzed enters a measuring path, which has two limiting surfaces located opposite each other. The first limiting surface is designed as a spherical mirror, and the second limiting surface is transparent to infrared radiation. An infrared radiation source and a radiation receiver are arranged at the second limiting surface such that a measuring beam emitted by the infrared radiation source is reflected on the mirror and then reaches the radiation receiver. The measuring beam now passes through the measuring path filled with the gas sample to be analyzed twice. The prior-art measuring cell has a length of about 7.5 cm and a width of about 3 cm and is suitable for the detection of carbon dioxide and carbon monoxide. The design of the measuring cell is especially advantageous for portable devices, because the electrical components, such as the radiation source and the radiation receiver, are fastened on one side of the measuring path and thus they can be connected to an electrical evaluating circuit in an especially simple and compact manner. In contrast, only optical components, namely, the spherical mirror, are arranged on the opposite side of the measuring path.

Difficulties arise in connection with the detection of gas components, e.g., methane, which require a markedly longer absorption path. The size of the measuring cell is, in general, not critical in the case of permanently installed devices, so that the necessary absorption path is reached with a correspondingly more largely dimensioned measuring path with a single reflection of the measuring beam.

SUMMARY AND OBJECTS OF THE INVENTION

The primary object of the present invention is to improve a measuring cell of this type such that while maintaining the outer dimensions of the measuring path, it is also suitable for detecting gases that require a longer absorption path.

To accomplish this object, a mirror surface effective for the measuring path is present in the area of the limiting surface at which the infrared radiation source and the radiation receiver are arranged, and the geometry of the optical component is dimensioned such that an at least fourfold pass of the measuring beam is present in the measuring path, utilizing the reflection of the radiation from the mirror surface.

The advantage of the present invention is essentially that doubling of the absorption path length is achieved due to the installation of an additional mirror surface in the area of the second limiting surface, without the outer dimensions of the measuring path having to be changed. Only the optical component arranged opposite the second limiting surface must be adapted to the new course of the measuring beam. Measuring cells can thus be built for detecting carbon dioxide and methane with the same housing body for the measuring path, and only a correspondingly adapted optical component and the mirror surface must be arranged at the housing body.

The mirror surface at the second limiting surface is advantageously arranged between the radiation source and the radiation receiver. Partial windows, through which the infrared radiation can enter and then leave the measuring path, are arranged in the area of the radiation source and of the radiation receiver at the second limiting surface. The mirror surface is arranged on one of the partial windows. Thus, only a correspondingly modified partial window with mirror surface arranged on it needs to be inserted in the housing body to connect the mirror surface to the housing body of the measuring cell.

One exemplary embodiment of the present invention is shown in the drawing and will be explained in greater detail below.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENT

Figure 1:
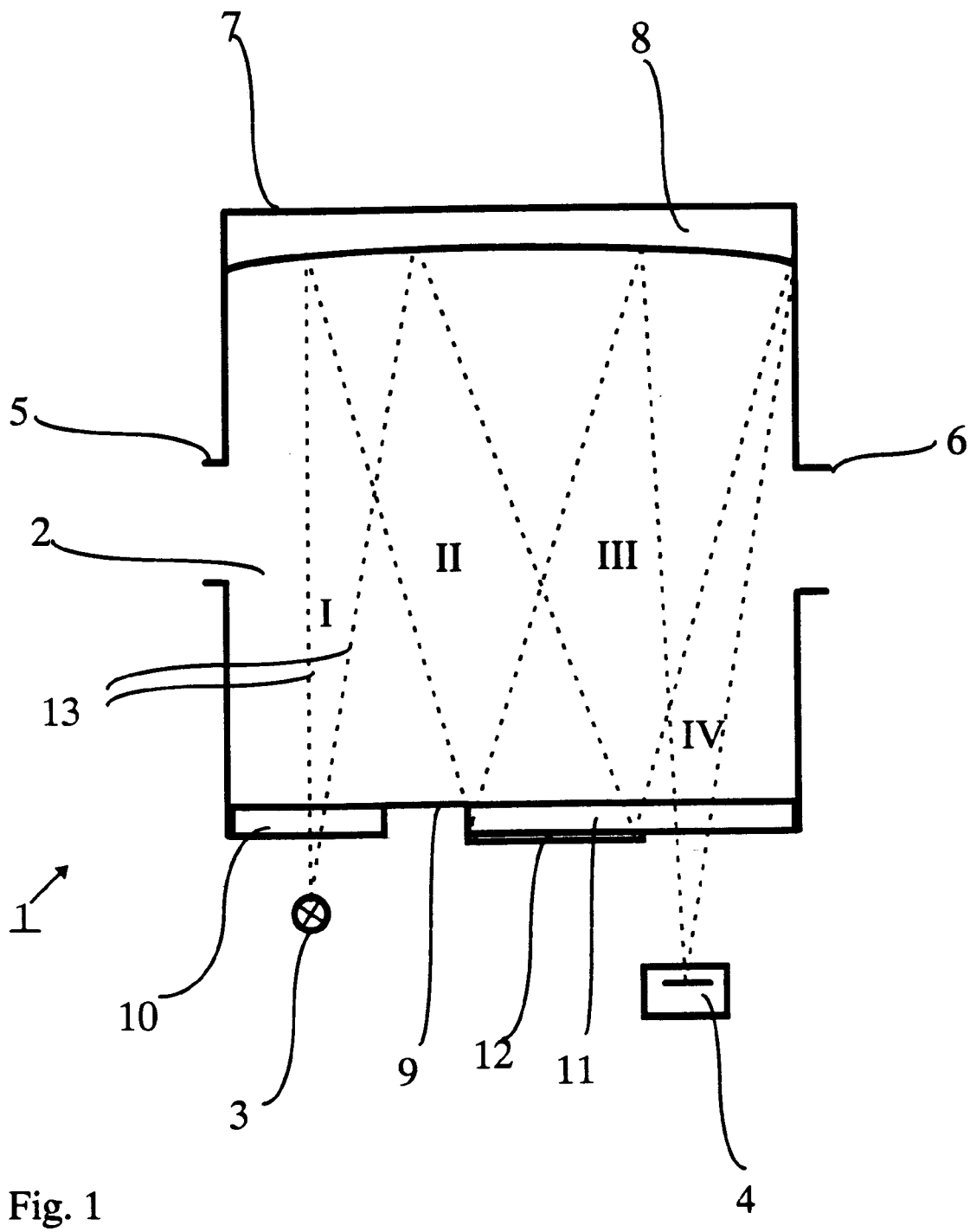
FIG. 1 is a schematic view of a measuring cell according to the present invention.

The measuring cell 1 shown schematically in FIG. 1 comprises a measuring path 2, which is filled with a gas sample to be analyzed, an infrared radiation source 3, and a radiation receiver 4. The gas sample enters the measuring path 2 at a gas inlet 5 and leaves the measuring path 2 at a gas outlet 6. The measuring path 2 has two limiting surfaces arranged opposite each other, wherein a spherical mirror 8 is arranged in an area of (at or adjacent to) a first limiting surface 7, a first partial window 10 is arranged in an area of (at or adjacent to) a second limiting surface 9, at the level of the radiation source 3, and a second partial window 11 is arranged at the level of the radiation receiver 4. The second partial window 11 is additionally provided with a mirror surface 12, which reflects the infrared radiation present in the measuring path. 2. The partial windows 10, 11 are designed as windows transparent to infrared radiation, with the exception of the area of the mirror surface 12, so that a measuring beam 13 emitted by the radiation source enters the measuring path 2 via the first partial window 10, it is reflected on the spherical mirror 8 and the mirror surface 12, and then leaves the measuring path 2 via the second partial window 11. The focal distance of the spherical mirror 8 is selected to be such that the measuring beam 13 falls on the radiation receiver 4 after four passes, which are designated by the Roman numerals I through IV in FIG. 1. Due to the fourfold pass of the measuring beam, absorption paths that are suitable for detecting methane in air are obtained.

The same housing body of the measuring path 2 may be used to detect a gas component with a shorter absorption path, and only the second partial window 11 is replaced with a design without mirror surface 12, and the spherical mirror 8 is replaced with a spherical mirror having a focal distance adapted to a twofold beam pass.

Figure 2:
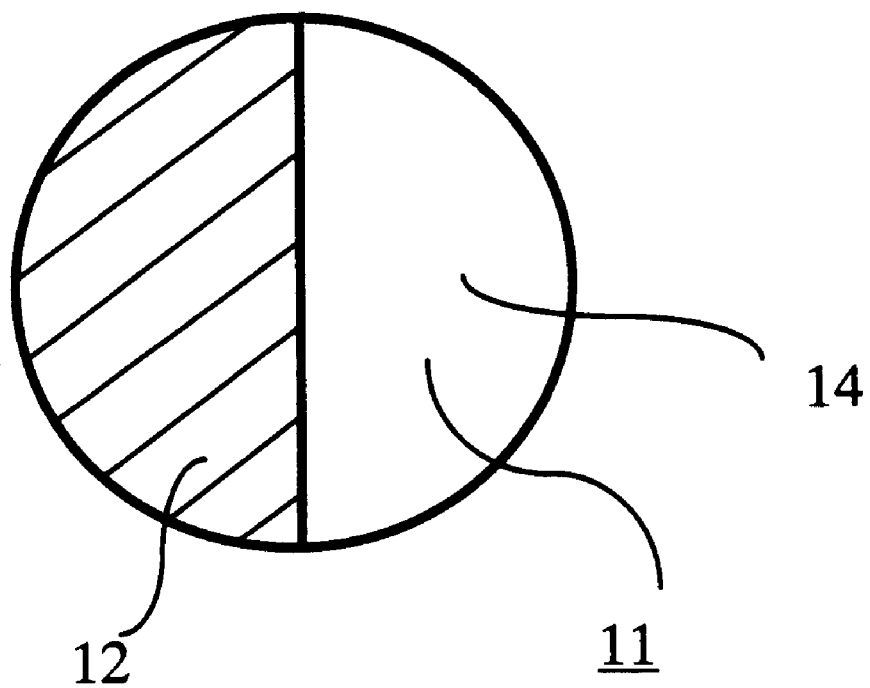
FIG. 2 is a top view of a partially metal-coated window.

FIG. 2 shows a top view of the second partial window 11 with the mirror surface 12 in the direction of view from the measuring path 2. The measuring beam 13 reflected by the spherical mirror 8, FIG. 1, is reflected on the mirror surface 12 and reaches the radiation receiver 4 after a fourfold pass through an area 14 of the second partial window 11 that is transparent to infrared light.

While specific embodiments of the invention have been shown and described in detail to illustrate the application of the principles of the invention, it will be understood that the invention may be embodied otherwise without departing from such principles.

What is claimed is:

1. A device for the analysis of a gas sample by means of infrared absorption, comprising:
   a cell defining a measuring path accommodating the gas sample, said cell having opposite first and second limiting surfaces enclosing the gas sample said cell defining a first partial window adjacent to said second limiting surface and said cell defining a second partial window;
   a focusing optical component arranged in an area of said first limiting surface;
   an infrared radiation source arranged in an area of said second limiting surface adjacent to said first partial window;
   a radiation receiver arranged in an area of said second limiting surface at a level of said second partial window such that a measuring beam emitted by said radiation source is directed through said optical component and through said second partial window and onto said radiation receiver; and
   a mirror surface active for said measuring path, said mirror surface being provided occupying a portion of said second partial window and being removable from said second partial window, a geometry of said optical component being dimensioned such that at least a fourfold pass of said measuring beam is present in said measuring path, utilizing a reflection of said measuring beam on said mirror surface.

2. The device in accordance with claim 1, wherein said mirror surface is arranged between said radiation source and said radiation receiver, opposite said optical component.

3. The device in accordance with claim 1, wherein said second limiting surface partial windows are transparent to infrared radiation, said partial windows being located in front of said radiation source and said radiation receiver with said mirror surface being arranged on said second partial window.

4. The device in accordance with claim 1, wherein said cell is for detecting methane.

5. A method for the analysis of a gas sample by means of infrared absorption, comprising the steps of:
   providing a cell defining a measuring path accommodating the gas sample, said cell having opposite first and second limiting surfaces enclosing the gas sample, said cell defining a first partial window adjacent to said second limiting surface and said cell defining a second partial window;
   providing a focusing optical component arranged in an area of said first limiting surface;
   providing an infrared radiation source arranged in an area of said second limiting surface adjacent to said first partial window and a radiation receiver arranged in an area of said second limiting surface at a level of said second partial window such that a measuring beam emitted by said radiation source is directed through said optical component onto said radiation receiver; and
   positioning a mirror surface in a position wherein it is active for said measuring path, in an area of said second limiting surface and in one of said first partial window and said second partial window; and
   dimensioning a geometry of said optical component such that at least a fourfold pass of said measuring beam is present in said measuring path, utilizing a reflection of said measuring beam on said mirror surface.

6. The method in accordance with claim 5, further comprising the steps of:
   arranging said mirror surface between said radiation source and said radiation receiver, opposite said optical component.

7. The method in accordance with claim 5, wherein said second limiting surface includes partial windows transparent to infrared radiation, said partial windows being located in front of said radiation source and said radiation receiver, said mirror surface being arranged on said second partial window.

8. The method in accordance with claim 7, wherein said mirror surface is arranged at said partial window located in front of said radiation receiver.

9. The method in accordance with claim 5, further comprising using said cell for detecting methane.

10. The method in accordance with claim 5, further comprising replacing one of said first and second partial windows with said mirror surface with another one of said first and second partial windows without said mirror surface and replacing said focusing optical component with a focusing optical component having a focal distance adapted to a twofold beam pass.

11. A device for the analysis of a gas sample by means of infrared absorption, comprising:
   a cell defining a measuring path accommodating the gas sample, said cell having a first limiting surface and an opposite second limiting surface enclosing the gas sample, said cell also having a gas inlet and defining a first partial window adjacent to said second limiting surface and said cell defining a second partial window adjacent to said second limiting surface;
   an infrared radiation source arranged in an area of said second limiting surface adjacent to said first partial window;
   a radiation receiver arranged in an area of said second limiting surface at a level of said second partial window;
   a mirror surface provided as a part of said second partial window and being removable and replaceable with a second partial window without said mirror surface;
   a focusing optical component arranged in an area of said first limiting surface with a geometry of said optical component being dimensioned such that at least a fourfold pass of said measuring beam is present in said measuring path, utilizing a reflection of said measuring beam on said mirror surface and being replaceable by a focusing optical component having a focal distance adapted to a twofold beam pass, a measuring beam emitted by said radiation source being directed through said optical component and through said second partial window and onto said radiation receiver.

12. The device in accordance with claim 11, wherein said mirror surface is arranged between said radiation source and said radiation receiver, opposite said optical component.

13. The device in accordance with claim 11, wherein said second limiting surface partial windows are transparent to infrared radiation, said partial windows being located in front of said radiation source and said radiation receiver with said mirror surface being arranged on said second partial window.

14. The device in accordance with claim 11, wherein said cell with said fourfold pass of said measuring beam is for detecting methane.

* * * * *